United States Patent
Sharma et al.

(10) Patent No.: US 6,446,517 B1
(45) Date of Patent: Sep. 10, 2002

(54) CONTROLLED PARTICLE DEPOSITION IN DRIVES AND ON MEDIA FOR THERMAL ASPERITY STUDIES

(75) Inventors: Vinod Sharma, Los Gatos; Debasis Baral, San Jose, both of CA (US)

(73) Assignee: Samsung Electronics Company (KR)

( * ) Notice: Subject to any disclaimer, the term of this patent is extended or adjusted under 35 U.S.C. 154(b) by 0 days.

(21) Appl. No.: 09/717,456

(22) Filed: Nov. 20, 2000

(51) Int. Cl.⁷ .............................................. G01N 17/00
(52) U.S. Cl. ..................................................... 73/865.6
(58) Field of Search ................................ 73/1.03, 1.05, 73/1.06, 1.07, 865.6, 865.9, 662, 663

(56) References Cited

U.S. PATENT DOCUMENTS

| | | |
|---|---|---|
| 3,558,831 A | 1/1971 | Prescott et al. |
| 4,110,802 A | 8/1978 | Ho et al. |
| 4,280,156 A | 7/1981 | Villette |
| 4,493,554 A | 1/1985 | Pryor et al. |
| 4,555,739 A | 11/1985 | Le Van et al. |
| 4,562,500 A | 12/1985 | Bygdnes |
| 4,630,926 A | 12/1986 | Tanaka et al. |
| 4,661,873 A | 4/1987 | Schulze |
| 4,673,996 A | 6/1987 | White |
| 4,703,376 A | 10/1987 | Edwards et al. |
| 4,731,777 A | 3/1988 | Yoshitoshi et al. |
| 4,739,425 A | 4/1988 | Dierkes et al. |
| 4,794,588 A | 12/1988 | Yoshitoshi et al. |
| 4,802,042 A | 1/1989 | Strom |
| 4,819,105 A | 4/1989 | Edwards |
| 4,866,553 A | 9/1989 | Kubo et al. |
| 4,870,519 A | 9/1989 | White |
| 4,890,172 A | 12/1989 | Watt et al. |
| 4,949,206 A | 8/1990 | Phillips et al. |
| 4,958,337 A | 9/1990 | Yamanaka et al. |
| 4,982,300 A | 1/1991 | Forbord |
| 5,004,207 A | 4/1991 | Ishikawa et al. |
| 5,029,026 A | 7/1991 | Stefansky et al. |
| 5,062,017 A | 10/1991 | Strom et al. |
| 5,128,822 A | 7/1992 | Chapin et al. |
| 5,159,508 A | 10/1992 | Grill et al. |
| 5,161,900 A | 11/1992 | Bougathou et al. |

(List continued on next page.)

FOREIGN PATENT DOCUMENTS

| | | |
|---|---|---|
| EP | 0 426 353 A2 | 5/1991 |
| EP | 0 463 752 A2 | 1/1992 |
| EP | 0 491 563 A2 | 6/1992 |
| EP | 0 582 464 A2 | 2/1994 |
| EP | 0 801 387 A2 | 10/1997 |
| FR | 2518-791 A | 6/1983 |
| GB | 2 050 670 A | 1/1981 |
| GB | 2 100052 A | 12/1982 |
| GB | 2 326 755 A | 12/1998 |
| JP | 632 344 55 | 9/1988 |
| JP | 3-83281 | 4/1991 |
| JP | 3-104079 | 5/1991 |
| JP | 09251769 A | 9/1997 |
| JP | 9-293370 | 11/1997 |
| WO | WO 93/10494 | 5/1993 |
| WO | WO 96/34390 | 10/1996 |

OTHER PUBLICATIONS

US 6,091,569, 7/2000, Allsup et al. (withdrawn)

Primary Examiner—Robert Raevis
(74) Attorney, Agent, or Firm—Irell & Manella, LLP; Jeffrey P. Aiello

(57) ABSTRACT

An environmental chamber that can be used to test a device under test such as a hard disk drive. The environmental chamber may include an electronically controlled shutter that controls the flow of controlled particles from a second chamber to a first chamber. The controlled particles flow to a device under the test located within the first chamber. The shutter can be closed when a predetermined threshold of contaminants is detected by the environmental chamber. This two-chamber method provides a stable and uniform density of particle environment around the drive.

14 Claims, 1 Drawing Sheet

U.S. PATENT DOCUMENTS

| | | |
|---|---|---|
| 5,167,167 A | 12/1992 | Tiernan, Jr. et al. |
| 5,175,661 A | 12/1992 | Mizuno et al. |
| 5,187,621 A | 2/1993 | Tacklind |
| 5,200,868 A | 4/1993 | Chapin et al. |
| 5,202,803 A | 4/1993 | Albrecht et al. |
| 5,214,549 A | 5/1993 | Baker et al. |
| 5,241,438 A | 8/1993 | Matsushima |
| 5,243,495 A | 9/1993 | Read et al. |
| 5,247,493 A | 9/1993 | Kime et al. |
| 5,262,913 A | 11/1993 | Stram et al. |
| 5,267,109 A | 11/1993 | Chapin et al. |
| 5,274,519 A | 12/1993 | Saito et al. |
| 5,287,235 A | 2/1994 | Cunningham et al. |
| 5,293,282 A | 3/1994 | Squires et al. |
| 5,307,018 A * | 4/1994 | Gadgil ............... 73/865.6 |
| 5,309,303 A | 5/1994 | Hsia et al. |
| 5,319,511 A | 6/1994 | Lin |
| 5,343,343 A | 8/1994 | Chapin |
| 5,347,414 A | 9/1994 | Kano |
| 5,365,389 A | 11/1994 | Jabbari et al. |
| 5,369,538 A | 11/1994 | Moe et al. |
| 5,381,701 A * | 1/1995 | Frankenthal et al. ....... 73/865.6 |
| 5,396,386 A | 3/1995 | Bolasna et al. |
| 5,396,387 A | 3/1995 | Murray |
| 5,402,290 A | 3/1995 | Daniel |
| 5,404,256 A | 4/1995 | White |
| 5,410,402 A | 4/1995 | Li et al. |
| 5,422,776 A | 6/1995 | Thorson et al. |
| 5,426,562 A | 6/1995 | Morehouse et al. |
| 5,442,638 A | 8/1995 | Awad et al. |
| 5,455,728 A | 10/1995 | Edwards et al. |
| 5,460,017 A | 10/1995 | Taylor |
| 5,463,527 A | 10/1995 | Hager et al. |
| 5,469,311 A | 11/1995 | Nishida et al. |
| 5,537,272 A | 7/1996 | Kazmierczak et al. |
| 5,546,250 A | 8/1996 | Diel |
| 5,555,144 A | 9/1996 | Wood et al. |
| 5,570,249 A | 10/1996 | Aoyagi et al. |
| 5,610,776 A | 3/1997 | Oh |
| 5,636,090 A | 6/1997 | Boigenzahn et al. |
| 5,663,853 A | 9/1997 | Park |
| 5,673,158 A | 9/1997 | Ichimura |
| 5,675,098 A * | 10/1997 | Hobbs ................ 73/865.6 |
| 5,677,813 A | 10/1997 | Yoshida et al. |
| 5,703,734 A | 12/1997 | Berberich et al. |
| 5,754,353 A | 5/1998 | Behrens et al. |
| 5,768,249 A | 6/1998 | Ro et al. |
| 5,781,373 A | 7/1998 | Larson et al. |
| 5,801,899 A | 9/1998 | Genheimer |
| 5,815,349 A | 9/1998 | Frater |
| 5,822,139 A | 10/1998 | Ayabe |
| 5,831,795 A | 11/1998 | Ma et al. |
| 5,844,754 A | 12/1998 | Stefansky et al. |
| 5,844,911 A | 12/1998 | Schadegg et al. |
| 5,875,067 A | 2/1999 | Morris et al. |
| 5,885,005 A | 3/1999 | Nakano et al. |
| 5,886,851 A | 3/1999 | Yamazaki et al. |
| 5,901,017 A | 5/1999 | Sano et al. |
| 5,926,347 A | 7/1999 | Kouhei et al. |
| 5,930,079 A | 7/1999 | Vera et al. |
| 5,930,080 A | 7/1999 | Frater et al. |
| 5,936,927 A | 8/1999 | Soga et al. |
| 5,969,901 A | 10/1999 | Eckberg et al. |
| 5,987,733 A | 11/1999 | Goss |
| 6,011,670 A | 1/2000 | Balsley, Jr. et al. |
| 6,034,941 A | 3/2000 | Ro |
| 6,046,883 A | 4/2000 | Miller |
| 6,084,744 A | 7/2000 | Genheimer et al. |
| 6,088,192 A | 7/2000 | Riener et al. |
| 6,088,194 A | 7/2000 | Imaino et al. |
| 6,088,202 A | 7/2000 | Kabasawa et al. |
| 6,154,360 A | 11/2000 | Kaczeus, Sr. et al. |
| 6,157,522 A | 12/2000 | Murphy et al. |
| 6,166,901 A | 12/2000 | Gamble et al. |
| 6,185,075 B1 | 2/2001 | Tsujino et al. |
| 6,185,807 B1 | 2/2001 | Kazmierczak et al. |
| 6,198,606 B1 | 3/2001 | Boutaghou et al. |
| 6,201,668 B1 | 3/2001 | Murphy |
| 6,205,005 B1 | 3/2001 | Heath |
| 6,226,143 B1 | 5/2001 | Stefansky |
| 6,226,152 B1 | 5/2001 | Tanaka et al. |
| 6,229,668 B1 | 5/2001 | Huynh et al. |
| 6,233,124 B1 | 5/2001 | Budde et al. |
| 6,239,943 B1 | 5/2001 | Jennings et al. |

\* cited by examiner

CONTROLLED PARTICLE DEPOSITION IN DRIVES AND ON MEDIA FOR THERMAL ASPERITY STUDIES

BACKGROUND OF THE INVENTION

1. Field of the Invention

The present invention relates to an environmental chamber used to test hard disk drives.

2. Prior Art

Hard disk drives include a plurality of transducers that are magnetically coupled to a number of rotating magnetic disks. The transducers write and read information by magnetizing and sensing the magnetic field of the disks. The transducers are typically integrated into heads that are mounted to suspension arms. The suspension arms are attached to an actuator arm. Information is typically stored within data sectors located in annular tracks of the disks. The actuator arm is attached to a voice coil motor that can be energized to move the transducers to different tracks of the disks.

Each head has an air bearing surface that cooperates with an air flow generated by the rotating disks to create an air bearing between the transducers and the disk surface. The air bearing prevents mechanical wear between the disk and the head. It is desirable to minimize the air bearing gap to optimize between magnetic coupling between the transducer and interference with the disk surface.

Disk drives are typically used in environments with varying temperatures, vibration, etc. Additionally, the disk drive may be exposed to contaminants that become deposited on the disk surfaces and degrade the performance of the drive. Most disk drives contain one or more filters that filter contaminates from the drive.

When designing a hard disk drive it is desirable to test design prototypes to determine certain performance characteristics during changing environmental conditions. Disk drives are typically placed within an environmental chamber that can heat, vibrate and provide a shock load to the drive.

BRIEF SUMMARY OF THE INVENTION

One embodiment of the present invention is an environmental chamber that contains a first chamber that is separated from a second chamber by a shutter. A device under test can be placed in the first chamber and exposed to contaminants introduced from the second chamber through the shutter.

DETAILED DESCRIPTION OF THE PREFERRED EMBODIMENT

Figure 1:
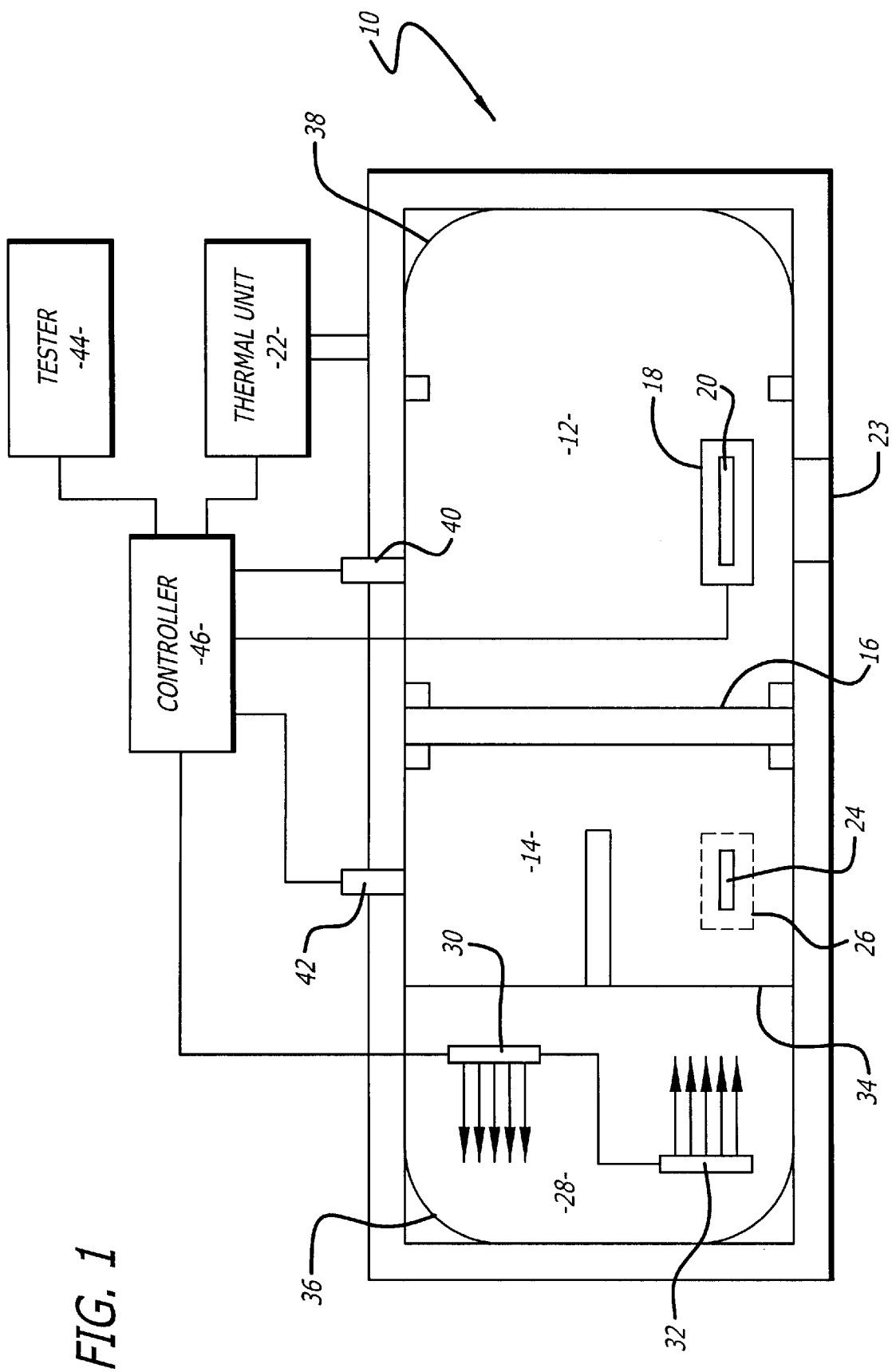
FIG. 1 is a schematic of an embodiment of an environmental chamber of the present invention.

The present invention includes an environmental chamber that can be used to test a device under test such as a hard disk drive. Controlled particles are placed at a known location. The environmental chamber may include an electronically controlled shutter that controls the flow of controlled particles from a second chamber to a first chamber. The controlled particles flow to a device under test located within the first chamber. The shutter can be closed when a predetermined threshold of controlled particles is detected by the environmental chamber. Particle density is monitored with a particle counter.

Referring to the drawings more particularly by reference numbers, FIG. 1 shows an embodiment of an environmental chamber 10 of the present invention. The environmental chamber 10 may include a first chamber 12 that is separated from a second chamber 14 by a shutter 16. The first chamber 12 may include a vibration table 18 that is adapted to support a device under test (DUT) 20. The device under test 20 may be a hard disk drive, or a component of a disk drive such as a disk. The vibration table 18 is configured to apply shock and vibration loads to the DUT 20. The first chamber 12 may also be coupled to a thermal unit 22 that can vary the temperature within the chamber 12. The chamber 10 may include a door 23 that allows the DUT 20 to be placed in, and removed from, the first chamber 12.

The second chamber 14 may include a port 24 that is in fluid communication with a reservoir of contaminants 26. The contaminants 26 may be compositionally identical to dust particles typically found in the working environment of a hard disk drive.

The environmental chamber 10 may further have a third chamber 28 that contains a first fan 30 and a second fan 32. The fans 30 and 32 generate a flow of air that passes through a porous wall 34 that separates the second 14 and third 28 chambers. A particle Counter can be used to monitor the density of particles.

The shutter 16 may be configured to switch between an open position and a closed position. In the open position the shutter 16 may allow contaminants to flow from the second chamber 14 to the first chamber 12. In the closed position the shutter 16 prevents fluid communication between the chambers 12 and 14.

The third chamber 28 may include a deflector 36 that induces a circulation of air throughout the second chamber 14 without creating "dead spots" in the corners of the third chamber 28. Likewise, the first chamber 12 may have a deflector 38 to circulate flow and prevent dead spots in the corners of the chamber 12.

The first chamber 12 may include a first chamber detector 40 that can detect a quantity of controlled particles within the chamber 12. The second chamber 14 may include a second chamber detector 42 that can detect a quantity of contaminants within the chamber 14. By way of example, the detectors 40 and 42 may be laser particle counters. The chamber 10 may have one detector 40 or 42, or both detectors 40 and 42.

The chamber 10 may include or be coupled to a tester 44 that performs test on the DUT 20 during varying environmental conditions. For example, the tester 44 may drive the hard disk drive to write and then read information, and then evaluate the results.

The environmental chamber 10 may include a controller 46 that is connected to the shutter 16, detectors 40 and 42, tester 44, vibration table 18, thermal unit 22 and/or fans 30 and 32. The controller 46 may contain a microprocessor, memory, drivers, etc. and other circuits required to control the environmental chamber 10. The chamber 10 may be controlled in accordance with a software routine performed by the controller 46. By way of example, the controller 46 may initiate a test routine by opening the shutter 16 to allow controlled particles to flow from the second chamber 14 to the first chamber 12. The controller 46 may close the shutter 16 when the detector 40 detects a predetermined quantity of contaminants within the first chamber 12. The controller 46 can then control the thermal unit 22 to vary temperature. The vibration table 18 may be activated, either subsequent, or simultaneous with, the variation in chamber temperature.

The tester 44 can then perform test to test the DUT 20. The controller 46 can open the shutter 16 for a time period(s) computed from the quantity of contaminants detected in the first chamber 12, contaminant density in the second chamber 14 and the flowrate generated by the fans 30 and 32.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Controlled particles can be replaced by fluids or particles suspended in fluids.

What is claimed is:

1. An environmental chamber to test a device under test, comprising:
    a first chamber adapted to contain the device under test;
    a second chamber that contains a contaminant;
    a shutter located between said first and second chambers, said shutter being adapted to switch between an open position and a closed position;
    a controller that can switch said shutter between open and closed positions;
    a fan that is coupled to said second chamber and which generates a flow of air that moves the contaminant from said second chamber to said first chamber when said shutter is in an open position; and,
    a first chamber detector that is coupled to said controller and can detect a quantity of the contaminant in said first chamber.

2. The environmental chamber of claim 1, further comprising a chamber detector that is coupled to said controller and can detect a quantity of the contaminant within said second chamber.

3. The environmental chamber of claim 1, further comprising a third chamber that contains said fan.

4. The environmental chamber of claim 3, wherein said third chamber contains a deflector.

5. The environmental chamber of claim 1, wherein said first chamber contains a deflector.

6. The environmental chamber of claim 1, further comprising a tester that can be coupled to the device under test.

7. The environmental chamber of claim 1, further comprising a thermal unit that is coupled to said first chamber.

8. The environmental chamber of claim 1, further comprising a vibration table that can vibrate the device under test.

9. An environmental chamber to test a device under test, comprising:
    a first chamber adapted to contain the device under test;
    a second chamber that contains a contaminant;
    a shutter located between said first and second chambers, said shutter being adapted to switch between an open position and a closed position;
    a fan that is coupled to said second chamber and which generates a flow of air that moves the contaminant from said second chamber to said first chamber when said shutter is in an open position;
    a first chamber detector that can detect a quantity of the contaminant in said first chamber; and
    a controller that is connected to said shutter, and said first chamber detector, said controller opens said shutter until said first chamber contains a predetermined quantity of contaminants.

10. The environmental chamber of claim 9, further comprising a second chamber detector that can detect a quantity of contaminants in said second chamber.

11. The environmental chamber of claim 9, further comprising a third chamber that contains said fan.

12. The environmental chamber of claim 11, wherein said third chamber contains a deflector.

13. The environmental chamber of claim 9, wherein said first chamber contains a deflector.

14. The environmental chamber of claim 9, further comprising a tester that can be coupled to the device under test.

* * * * *